(12) United States Patent
Pinotti

(10) Patent No.: US 8,316,794 B2
(45) Date of Patent: Nov. 27, 2012

(54) SYSTEM AND DEVICE FOR SELF-TANNING

(76) Inventor: Luciano Pinotti, Mantova (IT)

( * ) Notice: Subject to any disclaimer, the term of this patent is extended or adjusted under 35 U.S.C. 154(b) by 734 days.

(21) Appl. No.: 12/226,554

(22) PCT Filed: Apr. 19, 2007

(86) PCT No.: PCT/IT2007/000291
§ 371 (c)(1),
(2), (4) Date: Oct. 21, 2008

(87) PCT Pub. No.: WO2007/122659
PCT Pub. Date: Nov. 1, 2007

(65) Prior Publication Data
US 2010/0162951 A1    Jul. 1, 2010

(30) Foreign Application Priority Data

Apr. 21, 2006   (IT) .............................. MN2006A0032

(51) Int. Cl.
B05C 11/00 (2006.01)
B05B 1/28 (2006.01)
A45D 44/00 (2006.01)
A61H 33/06 (2006.01)
B05D 1/02 (2006.01)

(52) U.S. Cl. ........ 118/641; 118/642; 118/326; 118/695; 118/696; 118/643; 118/323; 132/333; 604/289; 604/290; 427/427.1

(58) Field of Classification Search .................. 118/326, 118/641–643, 313–316, 321, 695, 696, DIG. 7; 424/401, 59, 60, 78.02, 78.03; 132/200, 132/333; 604/289, 290; 239/207; 4/597; 427/421.1, 427.1
See application file for complete search history.

(56) References Cited

U.S. PATENT DOCUMENTS

| | | | | |
|---|---|---|---|---|
| 2001/0003283 A1* | 6/2001 | Laughlin | ....................... | 132/200 |
| 2002/0040721 A1* | 4/2002 | Laughlin | ....................... | 132/200 |
| 2003/0024946 A1* | 2/2003 | Severino | ........................... | 222/2 |
| 2004/0068789 A1* | 4/2004 | Pastorelli | ......................... | 4/596 |
| 2004/0073186 A1* | 4/2004 | Cameron | ....................... | 604/389 |
| 2004/0232257 A1* | 11/2004 | Venuto, Sr. | ................... | 239/200 |
| 2005/0120474 A1* | 6/2005 | Wegdam et al. | ................. | 4/596 |

* cited by examiner

Primary Examiner — Yewebdar Tadesse
(74) Attorney, Agent, or Firm — Thomas R. Vigil

(57) ABSTRACT

The present invention concerns a system and device for self-tanning of the type comprising a booth (2) in which two lateral walls (5) have one or more lamps (52) protected by gratings (51) arranged to warm the area inside the booth and to radiate the skin of a person in the booth. The booth is provided with a spraying device (11) for nebulizing a tanning substance. The device comprises a Second control panel (6) connected to a means of management envisaged for activating and governing the diverse functions of the device under the control of an operator or of a user. The system comprises a series of operative phases which envisage, for a person who undergoes a self-tanning session: entering the booth; pressing start on the control panel; the lamps switching on for a preset time and switching off; a tanning solution being sprayed, followed by the lamps being switched on a second time to dry the tanning solution; the lamps being switched off; the person leaving the booth.

12 Claims, 5 Drawing Sheets

SYSTEM AND DEVICE FOR SELF-TANNING

TECHNICAL FIELD

The present invention relates to a system and device for self-tanning particularly recommended for obtaining a golden colouring in a single session, by means of natural substances without being exposed to radiation from ultraviolet rays.

As it is known, nowadays fashion and lifestyle trends require people to always be neat and tidy, and healthy-looking with an attractive colouring, therefore in periods when it is not possible to tan naturally in the sun or there is no time and/or opportunities to do so, those who want tanned skin tend to frequent beauty centres and have treatments to obtain it.

At present, diverse tanning systems exist.

A first system consists of self-tanning creams or lotions which must be applied to the skin but give scarcely satisfactory results as they often leave marks on the skin if the cream is not applied uniformly, in addition to the fact that, in some cases, they can trigger allergic reactions on the skin. Furthermore, the treatment with the cream mentioned earlier cannot be carried out by a person autonomously as it is not possible to reach all the parts of the body easily and the colour that the skin assumes is not always golden but sometimes yellowish, therefore proves unpleasant.

A second system envisages the use of devices for the face and for the body with high and low-pressure lamps which emit ultraviolet rays A-B.

These devices produce the tan through the emission of ultraviolet rays that hit the skin, stimulating the production of melanin, which is the dark pigment that our body possesses to defend itself from overexposure to ultraviolet rays, and the colour of the pigment, melanin, gives people that attractive colouring that is known as tan. In practice, the devices mentioned above reproduce the same mechanism as the ultraviolet rays of the sun's light.

The system of tanning with ultraviolet rays, although extremely tried and tested, and utilized all over the world, has encountered certain problems.

A first problem arises from the fact that, for some time now, the World Health Organization has been criticizing the devices which use ultraviolet rays, above all the most recent ones, as their use seems to have multiplied cases of melanoma, in particular among very young people. In fact, the latest generation of tanning lamps work with a strong emission of ultraviolet rays to reduce the exposure times of each session and contain the number of sessions while maintaining the same level of tanning power. If tanning lamps were utilized which had the same quantity of ultraviolet rays emissions as the values recommended by the W.H.O., there would have to be a considerable increase in the exposure times and the number of sessions to undergo in order to obtain the so greatly desired tan, with consequent times and costs which people would probably not be willing to accept. Reinforcing the above, it should be noted that the Health Departments of countries like France, and Spain, and the state of California, have issued laws prohibiting minors to undergo UV sessions and advise other people not to undergo more than thirty sessions a year.

In addition, continuous exposure to ultraviolet rays stimulates cutaneous aging, the onset of erythemas, the appearance of marks on the skin and, furthermore, does not guarantee the attainment of the much sought after tan on all skin types.

A further problem encountered by the UV lamps emerges from the fact that they consume very large amounts of electric energy, therefore they have decidedly onerous running costs.

In addition to the above, the frenetic and busy lives we lead nowadays require us to change appearance, assuming an attractive colouring, without, very often, having the time to do so, therefore the possibility of changing skin tone in a short space of time is a need which is felt greatly by a large number of people.

To obviate the problems encountered by the devices with lamps which emit UV rays, for a while now, the industry has been seeking alternative solutions which allow a tan to be obtained without the use of UV lamps and to avert the problems of photoaging, erythemas, risk of melanomas and poor results on people with light skin, as mentioned earlier.

At present, booths are utilized whose structure features a series of holes into which nozzles are inserted and a tanning solution is discharged from these nozzles in a nebulized form. In the following 12-24 hours, the product spayed onto the skin triggers a reaction with a protein in the skin whose reaction gives the skin a particular colour that creates the tanned effect.

The system illustrated has demonstrated that it does not cause photoaging problems, or stimulate the onset of melanomas, and does not give rise to erythemas and burns, but nevertheless it has encountered a series of drawbacks.

A first drawback emerges from the fact that certain solutions that are sprayed onto skin contain coloured pigments to give a tanned effect immediately but these colouring substances tend to stain clothes and, when the person washes, they are washed off. A further drawback encountered is owed to the fact that the spraying of the tanning solution is not homogenous and uniform, in addition to the fact that the tanning solutions utilized at present contain solely DHA (Dihydroxyacetone) as the tanning factor. This substance gives the skin a yellowy orange tone that does not correspond exactly to the classic tan colour and is characteristically very dry, which means it is necessary to utilize considerable percentages of moistening elements in the solution, such as aloe, glycol, etc. The aforesaid use of softening substances renders the skin's absorption of the tanning solution sprayed on to it much slower. In fact, people are recommended not to wash and to try not to sweat for a period of at least 5-6 hours. To accelerate the absorption of the tanning solution towels are utilized, or fans, which do not render the tanning session particularly pleasant and, sometimes, give results that are not very good. As mentioned, a session with the currently available spray booths proves unpleasant during the autumn/winter period as the tanning solution is cold and the use of the fan increases the cold sensation on the damp skin.

A further drawback arises from the fact that a specific absorption system is lacking for the tanning solution, therefore the quantity of tanning solution utilized often proves either insufficient, with a reduced tanned effect, or excessive and therefore tends to give rise to marks.

A further drawback encountered is due to the fact that when the door of the booth opens, following a session, part of the tanning solution utilized, since it has been nebulized, is lost into the area surrounding the booth, with a consequent wastage of material and the need to carry out frequent cleaning operations in the area external to the booth. Furthermore, the interior of the booth also needs frequent cleaning operations as, since the sprayed solution is nebulized, it ends up, not only on the body of the person, but also on the walls of the booth and since it contains sugar-based substances, when the latter dry, they tend to stain the walls of the booth, with a decidedly unpleasant effect, and to obstruct the nozzle holes, rendering their subsequent use impossible after a while.

A further but not final drawback arises from fact that the booths used in the commonly known technique oblige the person to undergo a tanning session over the entire body.

The aim of the present invention is essentially to solve the problems encountered in the commonly known technique, overcoming the aforementioned drawbacks by means of a system and device for self-tanning featuring extreme ease of use and able to permit differentiated sessions to tan solely the face or the body or part thereof.

A further aim of the present invention is to realize a system and device for self-tanning able to permit the user to obtain a colouring identical to a traditional tan.

A further aim of the present invention is to realize a system and device for self-tanning able to permit the person to experience a pleasant session without the fastidious cold sensation even in autumn and winter.

A further aim of the present invention is to realize a system and device for self-tanning that permits the tanning solution to be better absorbed by the skin, drying quicker and utilizing an optimal quantity of solution without wastage and the presence of anti-aesthetic marks.

A further but not final aim of the present invention is to realize a system and device for self-tanning which is simple to realize and works well.

These aims and more besides, which will better emerge over the course of the present description, are essentially reached by a system and device for self-tanning, in accordance with the claims below.

Further characteristics and advantages of the present invention will better emerge from the detailed description which follows and the plates enclosed, which illustrate, purely in the form of a non-limiting example a system and device for self-tanning, in which.

Figure 1:
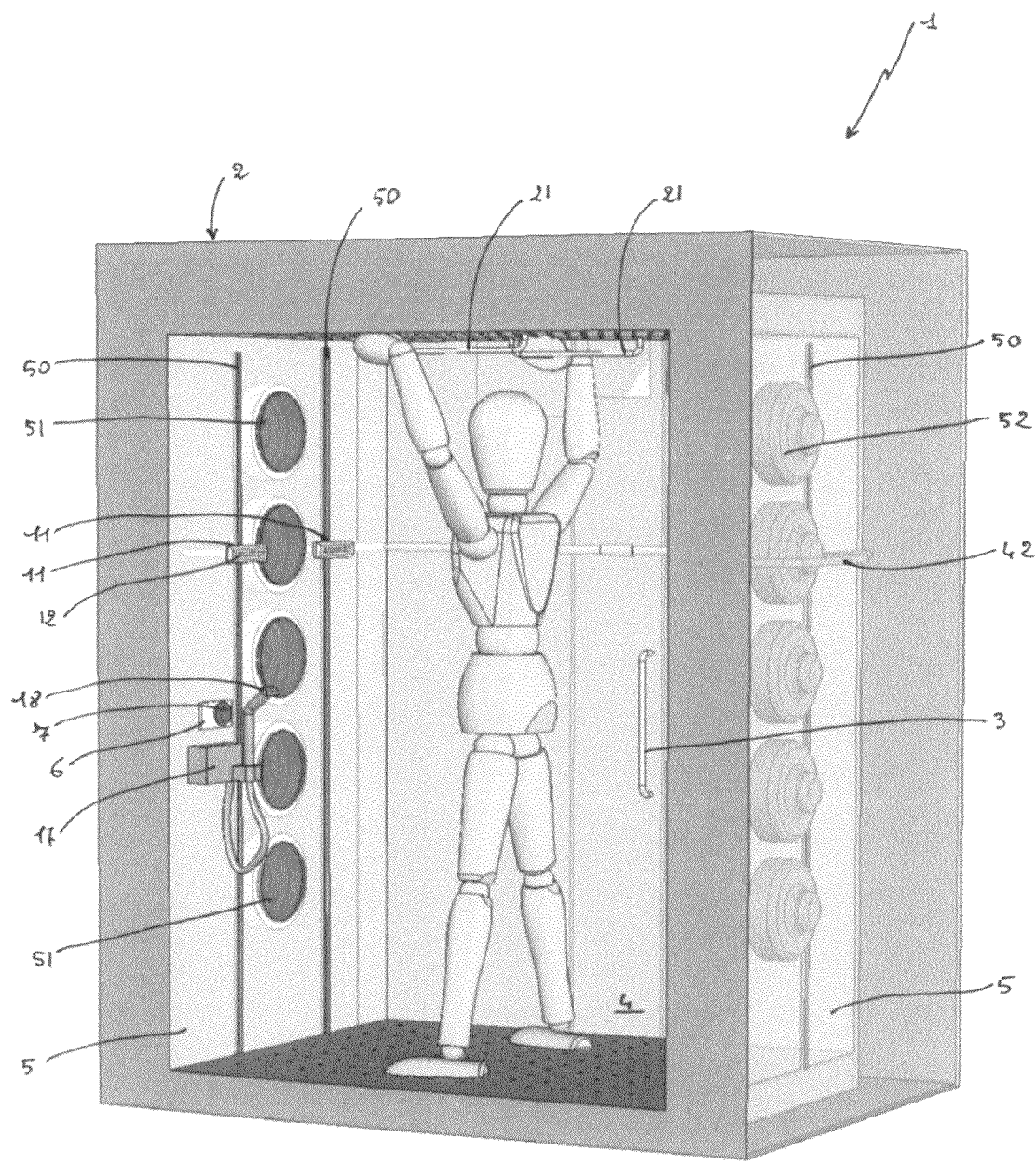
FIG. 1 shows, schematically and in a perspective view, a device for self-tanning according to the present invention utilized for the body.

With reference to the figures above, and in particular to FIG. 1, n. 1 denotes, as a whole, the device for self-tanning according to the present invention.

The device 1 in question comprises a booth 2 with one of the vertical walls featuring a door 3 to access said booth, a rear wall 4, which is in front of the door, and two lateral walls 5 fitted with a series of gratings 51. In greater detail, behind each grating 51 the presence is envisaged of one or more lamps 52 intended to warm up the area inside the booth in order to render it comfortable and pleasant and to radiate onto the person's skin so that the tanning solution utilized, once sprayed on, is absorbed by the skin more quickly and uniformly. In the present embodiment, lamps with infrared rays are utilized but lamps with similar characteristics can be used.

Figure 5:
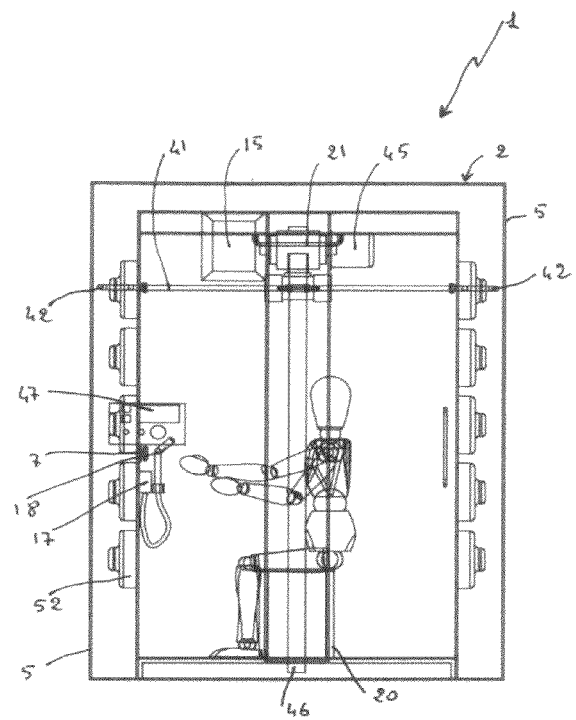
FIG. 5 shows a frontal view of the device in FIG. 2.
Figure 6:
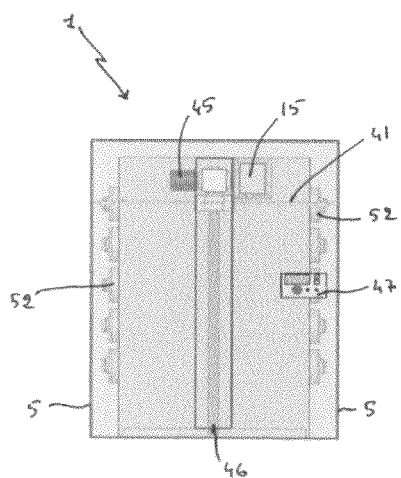
FIG. 6 shows a rear view of the device in FIG. 1.
Figure 7:
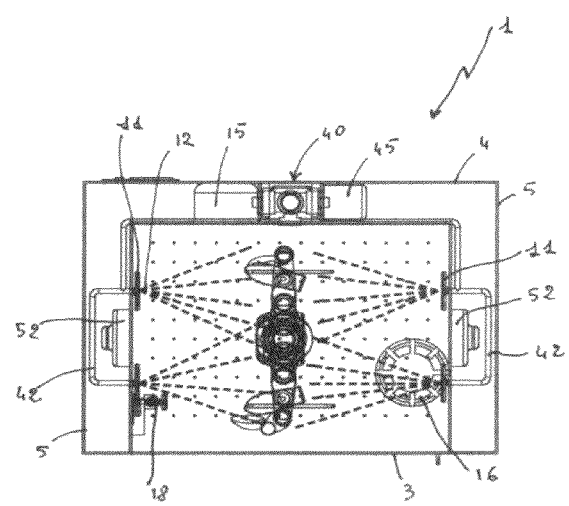
FIG. 7 shows an overhead view of the device according to the present invention in the operative condition.
Figure 8:
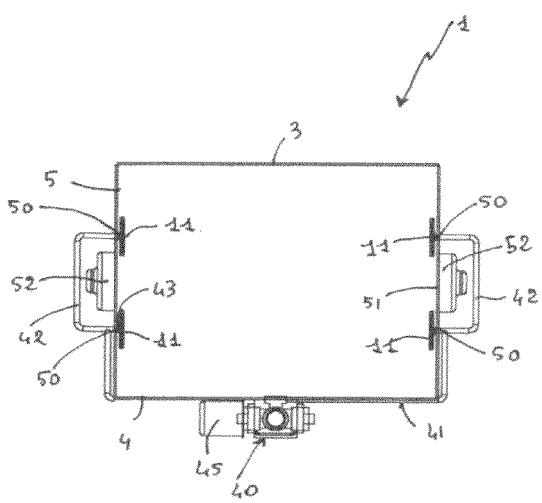
FIG. 8 shows an overhead view of the device in question.
Figure 9:
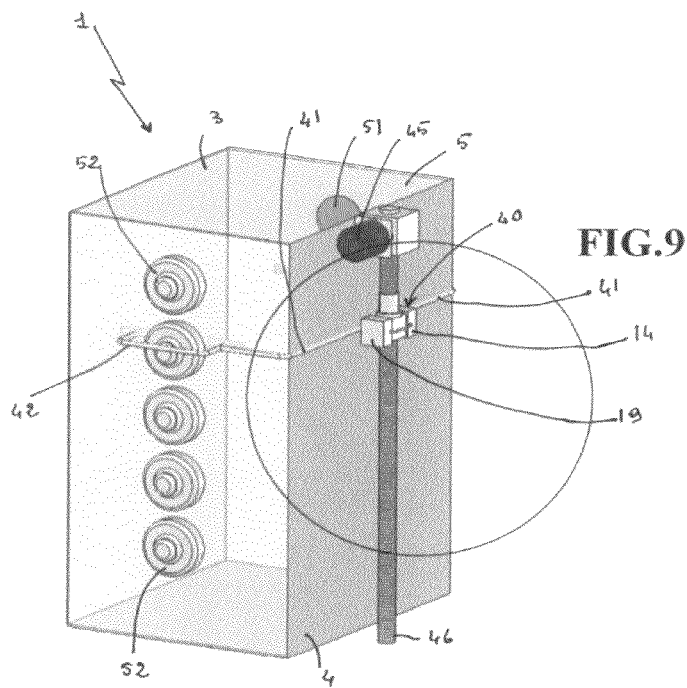
FIG. 9 shows, schematically and in a rear perspective view, the device for self-tanning.
Figure 10:
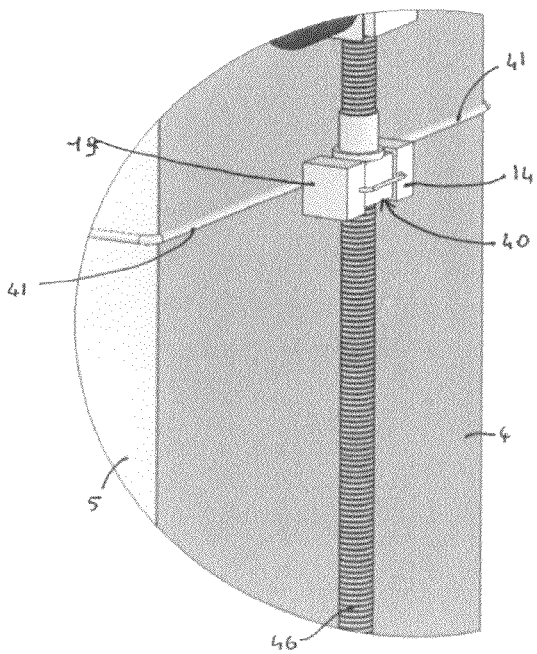
FIG. 10 shows a detail of the device in FIG. 9.

The device in question envisages that, externally to the rear wall 4, there are means of movement 40 present which are intended to make a rod 41 run, said rod being fitted with arms 42, each of which is envisaged to move parallel to a lateral wall 5, as shown in FIGS. 5 and 8. In particular, each lateral wall 5 features a pair of slits 50 into which the free ends 43 of each arm 42 enter. The ends 43 are fitted with a spraying device 11 equipped with nozzles 12 envisaged for nebulizing the tanning substance that is sprayed onto skin of the person in the interior of the booth as shown in FIGS. 1 and 7.

In greater detail, the rod 41 is moved from the bottom upwards and vice versa by a small motor 45 that drives an endless screw 46 which moves the rod 41 and the arms 42 up and down. Furthermore, if a user should bump into or interfere with the movement of the arms 42, a special safety device 47 cuts out their movement.

Figure 2:
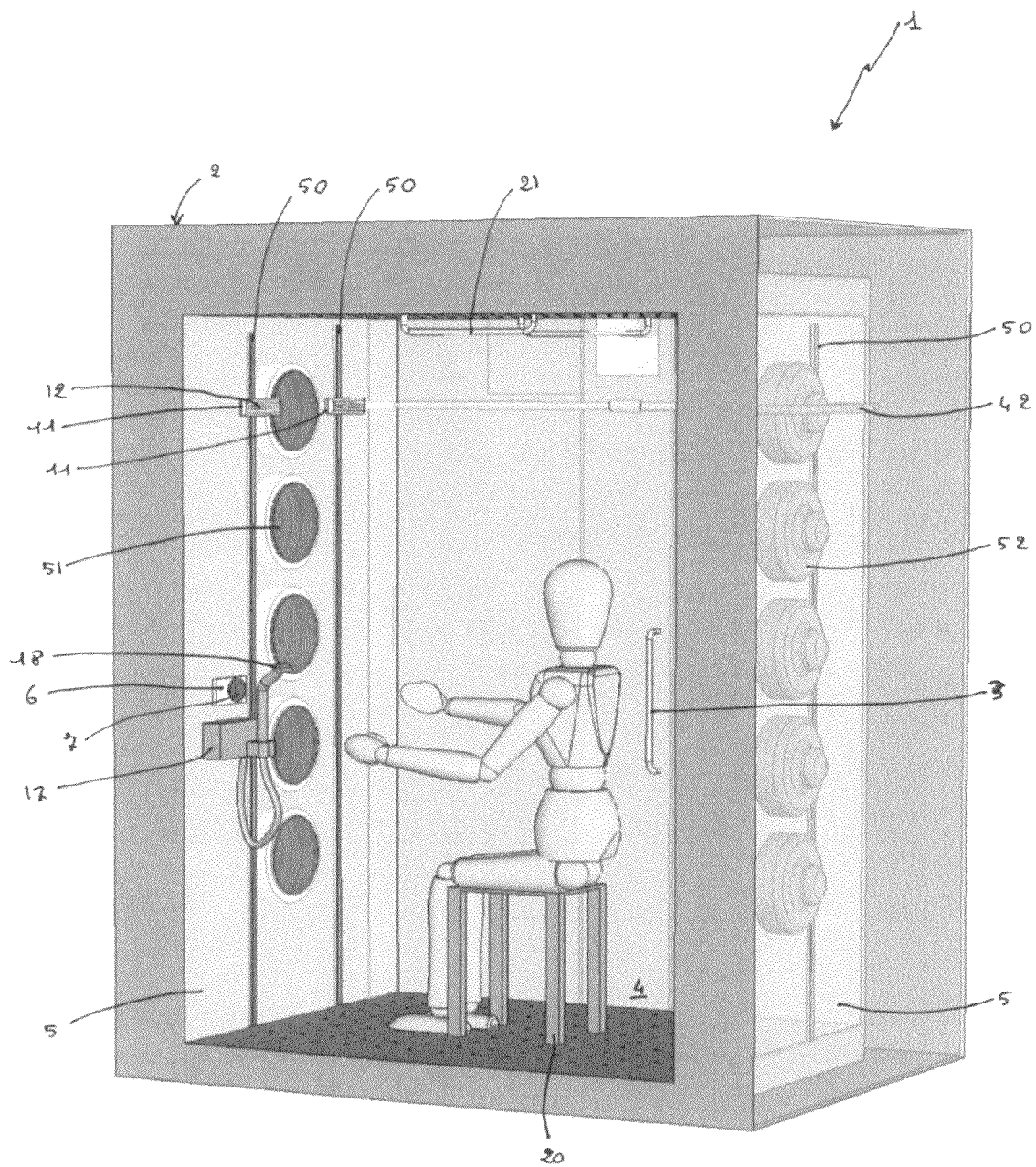
FIG. 2 shows, schematically and in a perspective view, the device for self-tanning of FIG. 1 utilized for the face.
Figure 3:
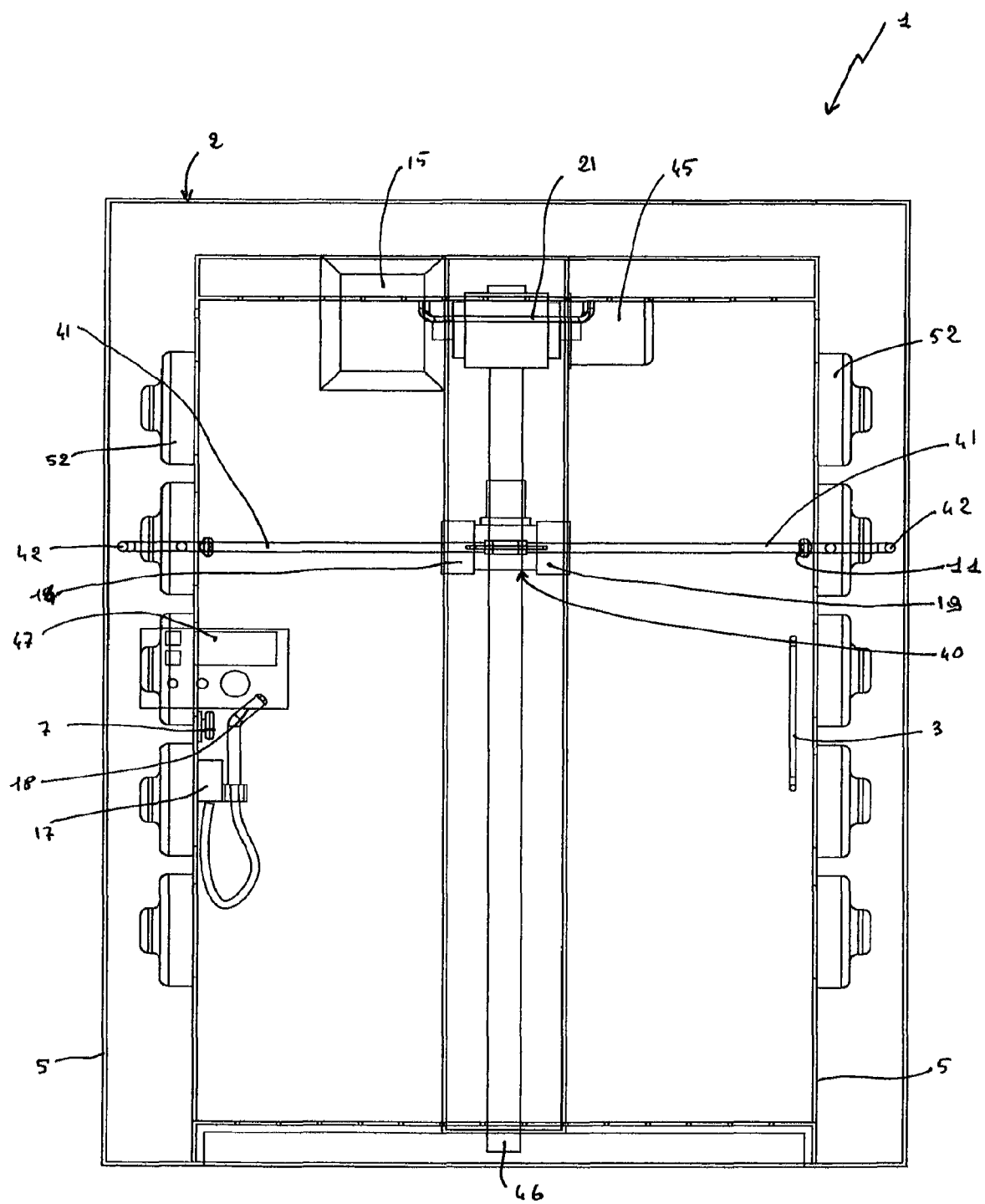
FIG. 3 shows, schematically and in a frontal view, the device for self-tanning in question.
Figure 4:
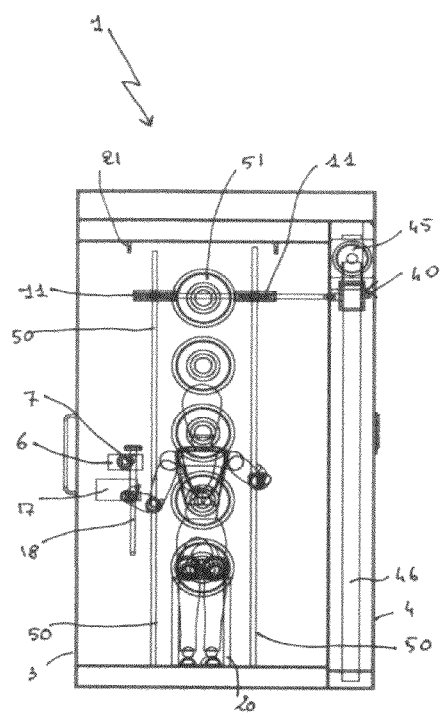
FIG. 4 shows a lateral view of the device in FIG. 2.

The device 1 features, in the interior of the booth, on a lateral wall 5, a control panel 6 connected to means of management the device envisaged for activating and governing the diverse functions of said device under the control of an operator or a user who pushes a start button 7 present on the control panel 6 shown in FIG. 2.

According to the present embodiment, the device 1 comprises a high-pressure pump 14 connected to a compressor which is envisaged for sucking up the tanning solution from a recipient 15 and transferring it to a pipeline connected with the spraying device 11.

In particular, connected to the pump 14 are the high-pressure tubes envisaged for connecting said pump to the spraying devices 11.

In agreement with the present embodiment, the device is fitted with a suction unit 16 located at the base of the booth and envisaged for collecting any of the tanning solution that is dispersed into the surrounding area.

In addition to the above and as shown in FIG. 5, the device 1 envisages, in the interior of the booth 2, the presence of a measuring recipient 17 located on the lateral wall, where the panel 6 is present, and containing the tanning solution. In greater detail, the measuring recipient 17 is, fitted with a button designed to discharge the tanning solution collected in a "container cup" provided into an spray-gun element 18, which is connected to the compressor so that the tanning solution comes out well nebulized. In particular, an operator, by means of a start button located on the spray-gun element, starts the nebulization of the tanning solution onto the face of a user, distributing the solution uniformly. The procedure illustrated above for the face can be repeated for any part of the body.

The measuring recipient and the spray-gun element are formed in such a way that the operator never has to touch the tanning solution or wear gloves.

Furthermore, the device comprises a warming device 19 for keeping the tanning solution at a preset temperature close to the that of the body. The warming device is constituted of an electric coil envisaged to maintain the tanning solution at body temperature. Likewise, any further commonly known type of warming system can be utilized to bring the tanning solution to the desired temperature and keep it there.

The device in question envisages that, in the interior of the booth, there is a seat 20 present on which a user sits to undergo a tanning session for the face only, as mentioned in earlier. Furthermore, the device is fitted, on the ceiling of the booth, with at least one handle 21 designed to permit the person to hold on to it or rest their hands on it to assume the correct solution application position.

The system for self-tanning according to the present invention comprises, for a person who wishes to undergo a session, the following operative phases:

person entering booth after putting on a protective cap for their hair and half-gloves that cover the palms of their hands only,
the start button on the control panel being pressed,
the lamps switching on for a preset time,
the lamps switching off, the tanning solution being sprayed,
the lamps switching on to dry the tanning solution on the skin for a preset time,
the lamps switching off,
person leaving booth.

During the tanning session, the person must remain still with their arms raised and their hand resting on the handle 21 and will be sprayed, contemporaneously, both in front and behind, as the arms with the spraying devices move from the top downwards, and vice versa if necessary, spraying the solution as they do so.

Once the person has left the booth, the suction unit sucks up the surplus nebulized solution and collects the solution that has fallen onto the booth's floor.

Following this predominantly structural description, the operation of the device in question is outlined below.

When a user decides to obtain a different look, they must undergo a session with the device according to the present invention. A session consists in a sequence of operative phases that comprise: entering the booth, pressing the "start" button on the control panel and positioning oneself frontally to a lateral wall.

At this point the lamps that warm up the area inside the booth will switch on, warming up, above all, the person's skin and making their pores dilate for a preset time of a few minutes. Once the warming phase has finished, the user simply has to raise their arms, rest their hands on the handle, wait for the tanning solution to be sprayed from the nozzles, and remain in position for a few minutes while the lamps switch on again so that the solution dries, penetrating the skin. The spraying device, located on the arms, starting from the top, will begin to discharge the tanning solution in a nebulized fashion, which will deposit on the user's skin, moving gradually downwards until it reaches the end of travel and, if necessary, the user will be able to request, via the control panel, for the spraying device to carry out a second route, from the bottom upwards, returning to the starting position and spraying the solution a second time. The lamps with infrared rays, in addition to warming the area inside the booth and preparing the user's skin, thereby opening its pores, facilitate the absorption of the tanning solution and its drying, quickly and in pleasant conditions. At this point the session ends and the user may leave the booth. If the user wishes, they may undergo a further session after a minimum time of approximately six hours to obtain a darker colouring. Actually, to accentuate the colour, it is possible to undergo two consecutive applications of the solution as mentioned earlier without any problems or contraindications. In fact, once the spraying device has reached the end of its travel downwards, it can move back up, still spraying, or it can stop and leave the lamps to switch on to allow the solution on the skin to be absorbed and dry, and then go back up, spraying again, and at the end, the lamps will switch on again.

In this way the present invention achieves the aims set.

The device in question features great ease of use and allows nebulization of the tanning solution to be effected onto the skin of the person in a homogeneous fashion and without wasting material.

Furthermore, the use of infrared lamps allows the tanning solution to be absorbed better and to dry quicker without the need to utilize towels or fans and without staining clothes, as occurs with the devices of the commonly known technique.

Advantageously, the use of infrareds has permitted an optimization of the quantity of tanning solution utilized, thereby averting stains or a limited result, as occurs with the commonly known technique. Furthermore, the use of infrareds renders the session pleasant even during the autumn/winter period. In particular, the infrareds increase the base metabolism and likewise microcirculation, therefore nutritional substances are carried to the skin and waste substances are more easily eliminated.

In particular, it is important to note that, due to the physical characteristic of the type of radiation at the frequency typical of infrared, the penetration of the ray is limited to the epidermal and dermal strata without going any deeper, which is what gives rise to the warming-up of the corneous stratum without causing the user any overwarming of the internal structures below, therefore there is no risk of burns.

The penetration of this radiation into the dermal strata causes a vasodilatation of the capillary microcirculation which causes a greater flow of blood, which can then both drain out waste substances and bring new nutrients designed to support and stimulate the metabolic reactions at the base of the tanning procedure.

In addition, with respect to other drying systems, the hot sensation caused by the warming is limited in time because it is superficial and the corneous stratum dissipates quickly, therefore no sweating occurs. In addition, the vasodilatation process lasts longer, therefore, the physical wellbeing effect, induced by the vasodilatation combined with the warming effect, is remarkable.

Advantageously, people with capillary fragility can undergo this treatment without any problems and without the problems that are encountered with the other systems in the commonly known technique.

Furthermore, the infrareds increase articular mobility and help eliminate muscular contractures therefore, following a session, in addition to having an attractive colouring, the person feels better, more active and fit.

In addition to the information highlighted above, the tanning solution utilized with the system and the device in question is transparent, does not contain colouring agents, and therefore does not stain the skin and does not soil clothes. In particular, the tanning solution contains DHA (Dihydroxyacetone) and a further self-tanning substance (Erythrulose). Furthermore, the tanning solution contains glycol, hydrating and emollient substances, and water.

The combination of the substances mentioned earlier, in preset proportions, has allowed the tanning effect to be radically changed, preventing the yellowy orange tone that occurred with the commonly known technique and allowing a colour to be obtained that reproduces the tanning effect identical to a traditional tan and gives the skin a bright look and a silky effect, apart from rendering it particularly soft.

Advantageously, with the solution utilized and the device in question, it is possible for the person who undergoes a session to wash after one hour, while a minimum of 5-6 hours are needed for the systems in the commonly known technique in order not to risk removing the colour.

A further advantage is due to the fact that the device allows the use thereof, both automatically and manually, to tan only certain parts of the body.

A further but not final advantage of the present invention is that the system and the device for self-tanning prove simple to realize and work well.

Naturally, numerous modifications and variants can be applied to the present invention while remaining within the scope of invention as defined by the characteristics herein.

The invention claimed is:

1. Device for self-tanning of the type comprising:
    A booth (2) having one vertical wall which features a door (3) for accessing said booth, a rear vertical wall (4) which is in front of the door and two lateral vertical walls (5), means of movement (40) intended to make a rod (41) run, said rod being fitted with arms (42) whose free ends (47) are provided with a spraying device (11) equipped with nozzles (12) designed to nebulize a tanning substance, a control panel (6) connected to means of management of the device envisaged for activating and governing the different functions of the device under the control of an operator or of a user and fitted with a start button (7), which is located inside the booth, on a lateral vertical wall (5), a high pressure pump (14) connected to a compressor which is envisaged for sucking up the tanning solution from a recipient (15) and transferring the tanning solution to pipes connected to the spraying devices (11), characterized i by the fact that it comprises:

a series of gratings (51) fitted on each lateral vertical wall (5) where, behind each grating (51), the presence of one or more infrared lamps (52) is envisaged that are intended to warm the area inside the booth and to radiate the skin of a person situated inside the booth;

said means of movement (40) and said rod (41) are located outside the rear vertical wall (4);

each of said arms (42) is intended to move parallel to each lateral vertical wall (5);

inside the booth (2), a measuring recipient (17) is located on the lateral vertical wall, where the control panel (6) is present, and containing the tanning solution, said measuring recipient (17) being fitted with a bottom designed to discharge the tanning solution that is collected in a container cup provided in a spray-gun element (18) which is connected to the compressor so that the tanning solution can exist well nebulized;

each lateral vertical wall (5) features a pair of vertical slits (50) into which the free ends (43) of each arm (42) enter.

2. Device for self-tanning according to claim 1, characterized by the fact
that said means of movement (40), which is adapted to move the rod (41) and the arms (42) up and down.

3. Device for self-tanning according to claim 1, characterized by the fact
that said device comprises a safety device (47), which is adapted to cut out the movement of the arms (42) in the event of a bump by a user or interference with the movement thereof.

4. Device for self-tanning according to claim 1, characterized by the fact
that high pressure pipes envisaged for connecting said pump to the spraying devices (11) are connected to the pump (14).

5. Device for self-tanning according to claim 1, characterized by the fact
that said device is fitted with a suction unit (16) located at the base of the booth and is envisaged for collecting any tanning solution that may be dispersed into the surrounding environment.

6. Device for self-tanning according to claim 1, characterized by the fact
that said device comprises a warming device (19) envisaged for keeping the tanning solution at a present temperature close to that of the body.

7. Device for self-tanning according to claim 6, characterized by the fact
that said device comprises, inside the booth, the presence of a seal (20) that is suitable for accommodating the user for a tanning session for the face only.

8. Device for self-tanning according to claim 1, characterized by the fact
that said warming device consists of an electric coil.

9. Device for self-tanning according to claim 1, characterized by the fact
that there is at least one handle (21) present on the roof of the booth, which is designed to permit a person to hold on to the handle or rest the hands on the handle to assume the correct solution application position.

10. The method for self-tanning utilizing a device according to claim 1, characterized by the fact
that said method comprises the following operative phrases:
a person entering the booth after putting on a protective cap for the hair and half-gloves that cover the palms of the hands only,
the start button on the control panel being pressed,
the lamps switching on for a preset time,
the lamps switching off,
the tanning solution being sprayed,
the lamps switching on a second time to dry the tanning solution on the skin for a preset-time preset,
the lamps switching off,
the person leaving the booth.

11. The method for self-tanning according claim 10, characterized by the fact
during the tanning solution spraying phase, the person remains with the arms raised and the hands resting on a handle present on the roof of the booth while they are sprayed, at the same time, both in the front and behind.

12. The method for self-tanning according to claim 11, characterized by the fact
the phase during which the lamps are switched on has a duration of a few minutes.

* * * * *